United States Patent
Liu

(10) Patent No.: US 11,324,417 B2
(45) Date of Patent: May 10, 2022

(54) MR COIL FRAME WITH BODY-FIXATION MEANS

(71) Applicant: Medical Intelligence Medizintechnik GmbH, Schwabmünchen (DE)

(72) Inventor: Rui Liu, Augsburg (DE)

(73) Assignee: MEDICAL INTELLIGENCE MEDIZINTECHNIK GMBH

( * ) Notice: Subject to any disclaimer, the term of this patent is extended or adjusted under 35 U.S.C. 154(b) by 0 days.

(21) Appl. No.: 16/407,862

(22) Filed: May 9, 2019

(65) Prior Publication Data

US 2019/0343420 A1 Nov. 14, 2019

(30) Foreign Application Priority Data

May 9, 2018 (EP) ..................................... 18171498

(51) Int. Cl.
*A61B 5/055* (2006.01)
*A61B 90/50* (2016.01)
*A61G 13/10* (2006.01)
*G01R 33/34* (2006.01)

(52) U.S. Cl.
CPC .............. *A61B 5/055* (2013.01); *A61B 90/50* (2016.02); *A61G 13/10* (2013.01); *G01R 33/34046* (2013.01)

(58) Field of Classification Search
CPC ...... A61B 5/0555; A61B 90/50; A61G 13/10; G01R 33/34046
See application file for complete search history.

(56) References Cited

U.S. PATENT DOCUMENTS

| | | | |
|---|---|---|---|
| 5,400,787 A * | 3/1995 | Marandos | A61B 5/055 600/422 |
| 5,730,745 A | 3/1998 | Schulte et al. | |
| 5,945,827 A | 8/1999 | Gronauer et al. | |
| 8,146,599 B2 | 4/2012 | Wilson et al. | |
| 9,581,664 B2 * | 2/2017 | Heismann | G01R 33/34007 |

FOREIGN PATENT DOCUMENTS

WO 2017089457 A1 6/2017

OTHER PUBLICATIONS

Extended European Search Report issued in European Patent Application 18171498.1, dated Oct. 31, 2018, 9 pages.

* cited by examiner

*Primary Examiner* — Gregory H Curran
(74) *Attorney, Agent, or Firm* — Quarles & Brady LLP

(57) ABSTRACT

A magnetic resonance coil frame includes a frame structure, forming in between a receiving space for at least a body portion of a recumbent patient located in a lying plane, wherein at least a first air-operated body-fixation means having a variable shape for immobilizing the body portion is arranged outside the lying plane at a side of the frame structure facing the receiving space. Thus, immobilizing a patient during magnetic resonance imaging and/or treatment can be improved.

15 Claims, 7 Drawing Sheets

MR COIL FRAME WITH BODY-FIXATION MEANS

CROSS-REFERENCES TO RELATED APPLICATIONS

This application claims the benefit of EP Application No. 18 171 498.1 filed May 9, 2018. The contents of that application are hereby incorporated by reference for all purposes as if set forth in their entirety herein.

FIELD OF THE INVENTION

The present invention relates generally to magnetic resonance image (MRI)—guided radiation therapy. In particular, the present invention relates to a magnetic resonance (MR) coil frame providing an improved stabilization and/or immobilization of a patient.

BACKGROUND OF THE INVENTION

Medical imaging is commonly used to assist in the diagnosis and/or treatment of patients. Magnetic resonance imaging (MRI) is an example of a medical imaging technology that can be performed during the diagnosis and treatment of tumors. Recently, machines have been developed on which MRI may be performed at the same time as diagnosing and irradiating the tumor, wherein radiation may be performed by e.g. a linear accelerator (LINAC)-system.

In order to be able to irradiate the tumor in the best possible way without compromising healthy tissue surrounding the tumor, high quality MR images are sought. For this, MRI may use local radio-frequency coils (RF coils) which, for example, increase a SNR (signal-to-noise ratio) to obtain better quality images. These RF coils may be carried by a magnetic resonance coil frame (MR coil frame).

Additionally, when using MRI for diagnosis and/or treatment, it is generally desired if the patient moves as little as possible. On the one hand, this may result in higher quality images during imaging since, for example, blurry artifacts within the images can be avoided. The higher the image acquisition time is, the more important it is that the patient moves as little as possible. On the other hand, during irradiation, e.g. during MR-LINAC treatment, the patient should move as little as possible, since any unexpected movement may lead to an unsafe situation. Such an unsafe situation may be that healthy tissue is being unintentionally irradiated.

In the prior art, e.g. U.S. Pat. No. 5,730,745 has proposed a fixation means in order to fix a patient during treatment and diagnosis. It describes a vacuum-assisted fixation means comprising a stereotactic frame and a mouthpiece attached to said stereotactic frame, wherein said mouthpiece having a surface for contacting a patient's hard palate. However, this may be uncomfortable for the patient due to position and/or material.

Further, U.S. Pat. No. 8,146,599 B2 has proposed another fixation means comprising a belt-like member formed of a pair of flexible sheets, each of which includes a clamp mechanism at its lower end. The belt-like member is arranged to be releasably mounted by those clamp mechanism to rails of a patient's support table. A disadvantage of this configuration is that the patient is strapped, which can be uncomfortable for the patient. Furthermore, the closing of the fixation means is also complicated and requires several mechanical steps. In addition, the belt makes it difficult to use a local RF coil.

Therefore, it remains a need to provide a sufficient fixation and positioning of the patient during imaging and/or radiation treatment of tumors which should be as comfortable as possible for the patient.

SUMMARY OF THE INVENTION

The present invention provides a magnetic resonance (MR) coil frame, in particular a body and/or anterior coil frame, which is adapted to carry a radio frequency (RF) coil. The MR coil frame comprises a frame structure, which can be provided in one piece or in several parts and which is preferably made from a non-conductive material in order to avoid conductive loops and $B_0$ field distortion. The coil frame is preferably adapted to support at least one RF coil and to maintain it at a predetermined distance from a body part of a patient. The frame structure may also be adapted to be placed on top of a support table and attached thereto. In this case, the frame can be moved along a longitudinal direction of the support table relative thereto and fixed in different positions, in particular relative to the patient. The top surface of the support table may define a lying plane for a recumbent patient to be diagnosed and/or treated within a MR-guided radiation system, in particular an MR scanner and/or MR-LINAC. Further, the frame structure forms in between a receiving space for at least a body portion of the recumbent patient located in the lying plane, wherein the body portion may be any part of a human or animal body. In order to stabilize and/or immobilize the body portion, at least a first air-operated, preferably vacuum-operated, body-fixation means having a variable shape and/or volume, which can be brought into contact with the body part, is arranged outside, e.g. in a distance to, the lying plane at a side of the frame structure facing the receiving space. In other words, the body-fixation means is not arranged within the lying plane and it is adapted to fix the body by contact and/or an abutment. By a variable shape can be understood, for example, that the body-fixation means may be flexible, moldable etc. In at least some embodiments, the body-fixation means may be configured as a cushion, bag, or the like.

Several advantages may be achieved with this configuration of the MR coil frame. On the one hand, the MR coil frame required anyway for carrying the RF coil fulfills a dual function, namely additionally as a carrier for a the body-fixation means. On the other hand, due to the variable shape and/or volume of the body-fixation means, a close contact with the body of the patient is achieved which results in a good fixation for stabilizing and/or immobilizing. Further, a variable shape and/or volume feels more comfortable for the patient than previous attempts at solution. Additionally, the body-fixation means can be used to insulate and/or cover the patient's body parts, such as e.g. arms or hands, in order to avoid forming a potential current loop, which can be formed by a pressure line of a blood pressure meter or the like.

In an embodiment of the invention, the frame structure may comprise a plurality of frame elements connected to each other. The frame elements may, for example, be inserted into one another and, if appropriate, fastened to one another in a detachable manner.

Thus, movement of the patient is further limited, and the frame may be made of several parts and can therefore be disassembled if required by the patient, for example, if the patient suffers from claustrophobia or the like.

According to a further embodiment of the invention, the frame structure carrying the body-fixation means may bridge-like span the lying plane. This means that the frame at least partially surrounds the lying body part, for example, in a domed manner.

Thus, the body-fixation means can also be attached so that the body part is fixed from one direction perpendicular or skewed to the lying plane. In particular, the body part can be fixed in the distance to the lying plane from a lateral side or can be pressed to the lying plane. In this case, the body-fixation means may be a kind of abutment for the lying plane.

In an embodiment of the invention, relative to a longitudinal axis of the receiving space, which longitudinal axis may be parallel to a body longitudinal axis of the patient to be immobilized, at least the first and a second body-fixation means may be arranged at substantially opposing frame elements on sides thereof facing the receiving space. In other words, at least two substantially opposing body-fixation means may be arranged with the patient in between. In this case, the two fixation means and a point of the lying plane may form a triangle, between which the patient to be fixed is located.

Thus, the patient can be fixed, for example, by a symmetrical arrangement, wherein one body-fixation means, namely the first or second body-fixation means, forms an abutment for the other. This further improves the fixation and makes it even more comfortable for the patient.

According to another embodiment of the invention, the first body-fixation means may be arranged at a first frame leg protruding from the lying plane and the second body-fixation means is arranged at a second frame leg protruding from the lying plane, and wherein the first and second frame legs are arranged symmetrically with respect to the longitudinal axes.

Thus, the MR coil frame has a free space between the frame elements, in particular between the legs, so that the patient feels more comfortable. On the other hand, the space can be used to accommodate the body-fixation means, the volume of which can be dimensioned accordingly larger. In addition, the MR coil frame is particularly stable and/or rigid to ensure a reliable fixation.

In another embodiment of the invention, the frame structure may have an internal air duct or a channel for passing a preferably separate air tube, which air duct or air tube at least extends between a first air connecting piece for an air pumping device and an internal volume of the respective body-fixation means. For this purpose, the internal air duct or channel may be formed as a hollow profile through which the air tube can be guided. To form the air duct, the frame elements may be made at least substantially airtight, e.g. by exact measurement, a coating, tight closing profile transitions between frame elements etc. The connection piece may be formed as a plug connection, screw connection or the like.

Thus, the frame can be formed as a hollow profile, and can additionally serve as a media supply for the body-fixation means in order to air-operate the internal volume thereof. This gives the MR coil frame a triple function and can avoid hanging pipes that could form current loops in the worst case, or at least complicate the placement of the patient.

According to an embodiment of the invention, the first air connecting piece may be arranged such that several of the body-fixation means can be operated by air simultaneously. Preferably, the first air connecting piece is arranged MR coil frame-sided. For example, the first air connecting piece may be an air passage, a valve or the like. For regulating the simultaneous operation of the body-fixation means different sections and/or parts of the MR coil frame may be fluidly adapted to one another. This can be done by adapting cross-sections, flow lengths, the provision of valves or other fluid mechanical components.

Thus, the time required for positioning the patient may be decreased. Additionally, the patient can be easier fixed symmetrically, which on the one hand is more comfortable for the patient and on the other hand improves the positioning for imaging and/or irradiation.

According to another embodiment, individual valves may be provided to individual ones of the body-fixation means. In at least some embodiments, the individual valves may be selectively controllable and/or selectively air operable. Preferably, the body-fixation means having individual valves may be configured to be selectively and/or individually controlled, especially in terms of supplying to and/or removing air from the body-fixation means. In at least some embodiments, e.g. one or more blocking elements as defined herein, other suitable valves or valve-like means may be used and/or modified for selective air actuation and/or selective air operation of the individual body-fixation means. For example, one or more blocking elements as described herein or other suitable means may be arranged in the frame structure, which may have one or more internal air ducts or a channels, associated with the one or more body-fixation means to which the air and/or vacuum is to be applied to. In at least some embodiments, the individual body-fixation means may be configured as a cushion, bag, or the like.

Thus, e.g. a vacuum or an air filling may be provided to just one body-fixation means of a plurality of body-fixation means. Further, the body-fixation means may be selectively controlled, so that a first body-fixation means may be operated while a second body-fixation means is not operated. This may allow to give more options when moulding the body-fixation means to a patient's body. Further, this may allow a greater control over which body-fixation means the air and/or vacuum is applied to.

In another embodiment of the invention, the frame elements may at least partially have a fluidically communicating connecting and/or transition portion, via which the frame elements are detachably connected to each other. For example, the hollow frame elements may be dimensioned so that they can be plugged into each other. For securing the frame elements to each other, a spring bolt or the like may be provided at the one the frame element and an engaging hole may be provided at the other frame element.

Thus, not each frame element requires its own air connecting piece so as to be connected to the air pump, but a common air connecting piece can be provided at only one frame element, from where it may be communicate over the frame structure.

According to an embodiment of the invention, the internal air duct or the separate air tube may be fluidically interrupted when the respective frame elements are disconnected. For this purpose, the frame elements may be detachable connected to each other. When using an air tube, the air tube can also be formed in several parts, wherein a connecting portion between two air tube parts is arranged approximately in the region of a connecting portion of the frame elements, so that the air tube is also interrupted when releasing the frame elements. If the hollow profile of the frame elements itself forms the internal air duct, the air flow is interrupted immediately, regardless of whether a negative pressure or a positive pressure relative to the ambient pressure of the frame environment is used.

Thus, if patient feels uncomfortable and disconnects the frame elements, or medical personnel disconnects the frame elements, the air connection to the body-fixation means is also interrupted, so that the air-operated fixing of the body-fixation means is at least loosened. This increases the reliability or represents a security feature.

In another embodiment of the invention, the at least first body-fixation means may be fluidically connectable or connected to an air pumping device via a second air connecting piece. Preferably, the second air may be arranged body-fixation means-sided. The pumping device may be a vacuum pump that provides a negative pressure relative to the ambient pressure.

Thus, the body-fixation means can be operated over the frame by means of the pumping device.

According to an embodiment of the invention, at least a portion providing the variable shape of the body-fixation means may be formed from a flexible material having air or gas tight properties. The material may have an attenuation of less than 2% for X-ray radiation between 1.8 and 8 MeV. Preferably, the material may have a minimum impact on homogenous $B_0$ magnetic field, e.g. $B_0$ distortion may be <0.25 ppm inside the MR imaging volume, and shall not generate unacceptable distortion within the image. The material may be selected from: foam, expanded polypropylene foam, polyurethane foam, polyamide foam, polyether ether ketone (PEEK) foam and biocompatible surface foam based on EVA (ethylene-vinyl acetate).

Thus, the cushion can hold the air or a vacuum for a long time. Additionally, impact on the image by the body-fixation means can be reduced to a minimum.

In another embodiment of the invention, at least a portion providing the variable shape of the body-fixation means may be formed as a vacuumable cushion attachable to the frame structure. The cushion may be molded to the patient's anatomy and allows the patient to be positioned in exactly the same position for imaging and treatment and for each subsequent treatment fraction. The frame-side connection piece may be uniform so that interchangeability of the cushions is given.

Thus, a single MR coil frame can be provided with differently shaped or different sized cushions that are attached as needed or detached.

In another embodiment of the invention, the flexible cushion is made of an impermeable and insulation material having a flowable filling material to ensure a conformal, patient specific mold. The material may be selected from: foam, expanded polypropylene foam, polyurethane foam, polyamide foam, polyether ether ketone (PEEK) foam and biocompatible surface foam based on EVA (ethylene-vinyl acetate). The flowable filling material may be, for example, grains, balls or the like, preferably made of polystyrene or the like. In order to be able to assign a patient-specific mold, the body-fixation means may comprises a machine-readable label, such as an RFID tag.

Thus, molding the body-fixation means to the patient's anatomy and thus immobilizing the patient in a specific position can be further improved. In addition, the cushion can keep its shape better by the filling material.

In another embodiment of the invention, the body-fixation means may have an additional filling nozzle that opens to or communicates with the internal volume of the body-fixation means for filling the filling material.

Thus, the filling material, the type and/or amount of filling material may be changed. For example, material type, ball size and amount such that the overall vacuum cushion stiffness, density, thickness, radiation beam attenuation, dose dosimetry can be adjusted. Therefore, such personalized vacuum cushion could be used to reduce undesired radiation on different body parts for each patient case.

According to a further embodiment of the invention, the body-fixation means is attached to the frame structure via at least one attachment means having an internal air duct or a channel for passing an air tube. Preferably, the attachment means may form an integrated component, i.e. a one-piece component, with the second air connecting piece as explained above. Further preferably, the MR coil frame may have a counter-fastening means.

Thus, the structural design of the body-fixation means is as simple as possible, as it can be air-operated and attached by the very same means.

In another embodiment of the invention, the at least one attachment means may be arranged on a side of the body-fixation means facing away from the receiving space. In other words, it may be arranged so that the body-fixation means is between the MR coil frame and the attachment means.

Thus, the attachment means does not press on the patient and increases comfort accordingly.

According to an embodiment of the invention, the at least one attachment means is a fastening nut made of a non-conductive material. Preferably, the fastening nut may be made from a suitable plastic. Further, the fastening nut may be integrated in the material of the body-fixation means, for example by multi-component injection molding, in which the fastening nut may be inserted as a preform in the injection mold of the body-fixation means. For this purpose, the body-fixation means may have on its side facing away from the receiving space a stiffener, which can also be formed by multi-component injection molding, wherein the part providing the variable shape and/or volume is made from a first e.g. plastic material and the part holding the attachment means is made from more rigid or stiffer, second e.g. plastic material. Further preferably, as a counter-fastening means a thread may be incorporated or a threaded insert may be inserted into the MR coil frame.

Thus, the influence on the images during MRI can be minimized by the use of the non-conductive material. In addition, the attachment to the MR coil frame can be made simple, the nut can be attached hand-tight without additional tools.

The body-fixation means may be identical to each other. Accordingly, the attachment means and the counter-attachment means of the frame elements may also be identical to each other. Alternatively, they may vary depending on the anatomy of the patient. Also, if the body-fixation means are filled with a filling material, the type and/or amount of filling material may vary between the single body-fixation means. For example, the material type, ball size and amount can be varied such that the overall vacuum cushion stiffness, density, thickness, radiation beam attenuation, dose dosimetry can be adjusted. Therefore, such personalized vacuum cushion could be used to reduce undesired radiation on different body parts for each patient case.

It should be noted that embodiments as described above may be combined with respect to each other so as to gain a synergetic effect, which may extend over the separate technical effects of the single features. Exemplary embodiments of the present invention will be described in the following.

BRIEF DESCRIPTION OF THE FIGURES

Exemplary embodiments of the invention will be described in the following with reference to the following figures.

The figures are merely schematic representations and serve only to illustrate the invention. Identical or equivalent elements are consistently provided with the same reference signs.

DETAILED DESCRIPTION OF EXEMPLARY EMBODIMENTS

In the following, a detailed description of exemplary embodiments will be given to explain the invention in more detail.

Figure 1:
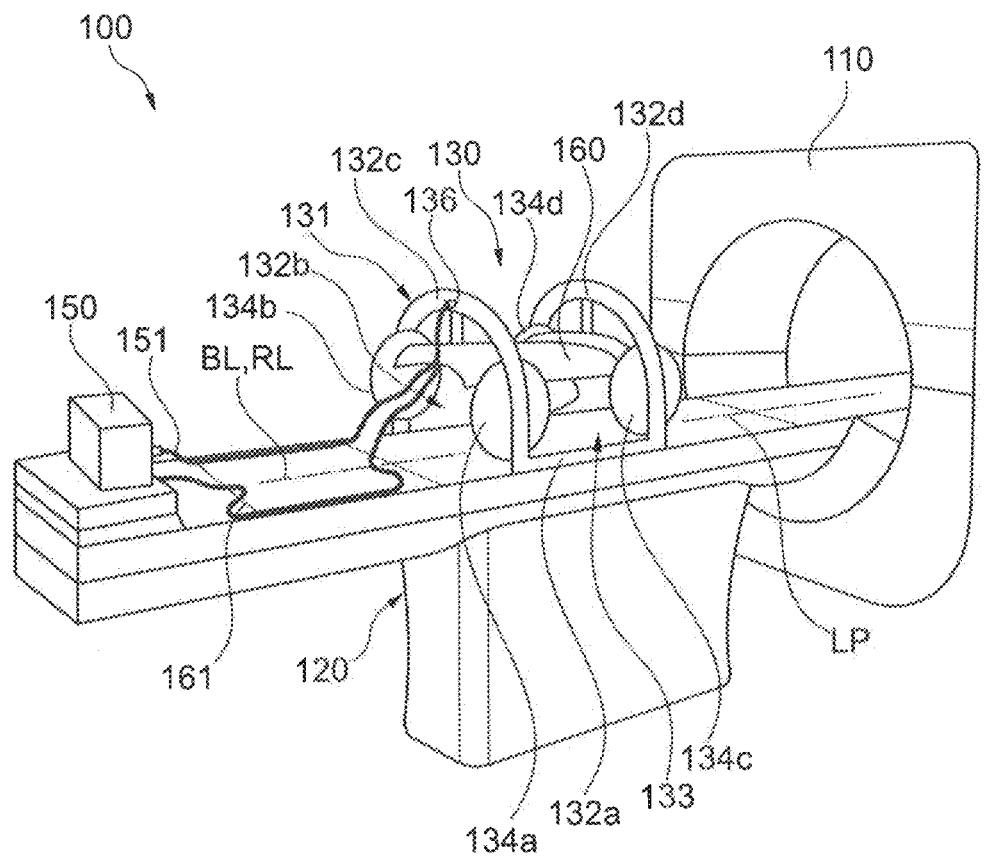
FIG. 1 is an MR-guided radiation system having a support table and an MR coil framed which is arranged on it, according to an embodiment of the invention.

FIG. 1 illustrates schematically an MR-guided radiation system 100 which comprises an MR scanner 110, a support table 120 standing on a floor surface, an MR coil frame 130 arranged on the support table 120, an air pumping device 150 fluidically connected to the MR coil frame 130 via a separated air tube 151, and an RF coil 160 carried by the MR coil frame 130 and extending substantially in parallel to a top surface of the support table 120. The RF coil 160 is communicationally connected via a communication cable 161.

The top surface of the support table 120 defines a lying plane LP for a recumbent patient (not shown) and can optionally be moved in and out the MR scanner 110. The MR coil frame 130 comprises a frame structure 131 having a plurality of frame elements 132a-d detachable connected to each other. The frame structure 131 is supported on the support table 120 and spans the lying plane LP like a bridge, in that the frame elements 132a, 132b supported on the support table 120 extend away from the lying plane LP and the frame elements 132c, 132d extend over the lying plane LP like an arch. Accordingly, frame elements 132c, 132d form a cross connection expanding over the support table 120. A receiving space 133 is formed between an inner side of the frame structure 131 and the lying plane LP for at least a body portion of the recumbent patient. As shown in FIG. 1, a central longitudinal axis RL of the receiving space 133 is parallel to a central longitudinal axis of the lying plane LP or a body central longitudinal axis BL of the patient to be immobilized, respectively.

Outside the lying plane LP, e.g. in a distance or adjacent to it, the frame structure 131 comprises or carries, respectively, one or more air-operated body-fixation means 134a-d, wherein in this embodiment four body-fixation means 134a-d are provided by way of example. Each of the body-fixation means 134a-d is made from a flexible material and thus has a variable shape or volume. They are each attached to one of the frame elements 132a, 132b each having two legs, so that each body-fixation means 134a-d is arranged at one of the legs, as shown in FIG. 1. In order to be arranged between the patient and the frame structure 131, the body-fixation means 134a-d are arranged on a side of the respective frame element 132a, 132b, which faces the receiving space 133. In particular, the first body-fixation means 134a is arranged at the first frame leg protruding from the lying plane LP, the second body-fixation means 134b is arranged at a second frame leg protruding from the lying plane LP, wherein the first and second frame legs are arranged symmetrically with respect to the longitudinal axes RL, BL. Likewise, the third body-fixation means 134c is arranged at the third frame leg opposes the first body-fixation means 134a and the fourth body-fixation means 134d arranged at the fourth frame leg opposes the second body-fixation means 134b. In summary, the body-fixation means 134a-d are symmetrically arranged relative to the central longitudinal axis RL of the receiving space 133 and the body central longitudinal axis BL.

Figure 2:
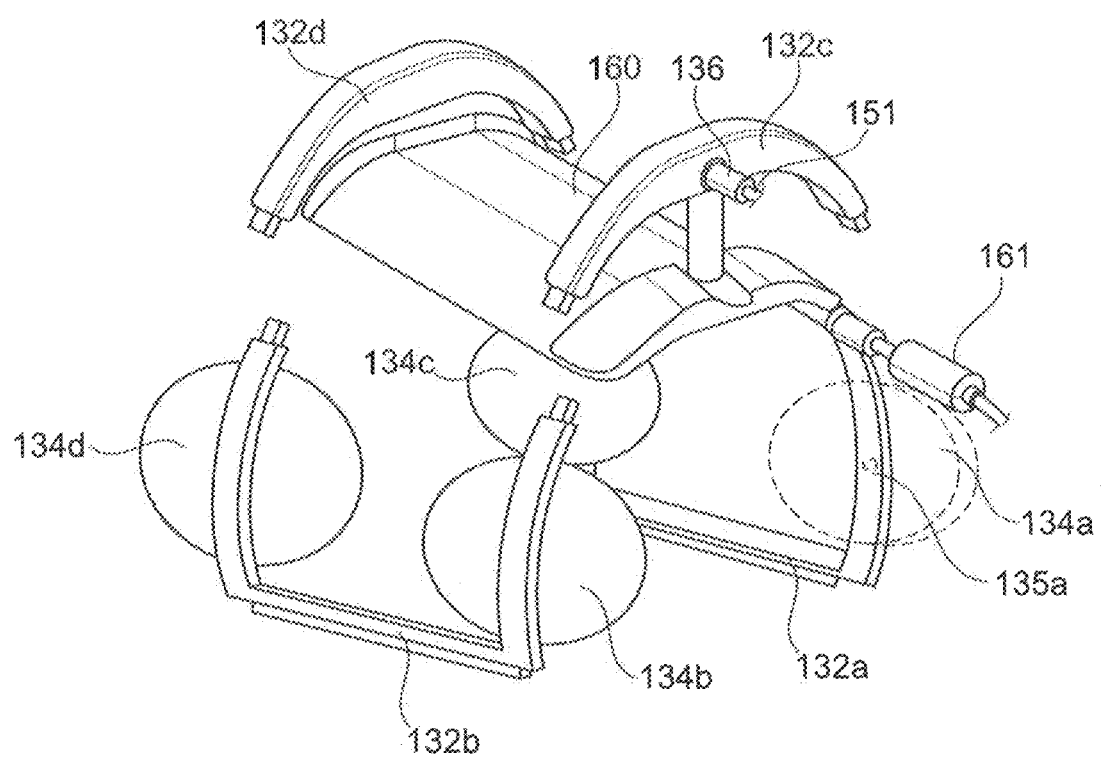
FIG. 2 is an MR coil frame having body-fixation means according to an embodiment of the invention.

FIG. 2 shows schematically the frame structure 131 of FIG. 1 as an individual component in a kind of exploded view. As shown, the frame structure 131 comprises the plurality of frame elements 132a-d which are connected to each other. By way of example, the frame elements 132a-d are pluggable in one another and can be fastened to each other by any suitable fastening means, such as a spring bolt and a corresponding engaging hole or the like. Using the example of the first body-fixation means 134a, it is indicated through dashed lines that the respective body-fixation means 134a-d are attached to the frame structure 131 in a detachable and in a fluidic manner by a respective attachment means 135a-d (see also FIG. 5 for more details). As it will be described in more detail below, the frame elements 132a-d are formed from a hollow profile, which is a hollow rectangular profile here. Thus, the body-fixation means 134a-d are fluidically connected to each other via the attachment means 135a-d and the hollow frame elements 132a-d. In addition, the body-fixation means 134a-d are fluidically connected to a MR coil frame-sided first connecting piece 136 that forms a connection to the air tube 151 of the air pumping device 150, wherein between the frame structure 131 and the air pumping device an air pipe extends (see FIG. 1). By way of example, the first connecting piece 136 is arranged at the frame element 132c that extends over the lying plane LP. Thus, the first connecting piece 136 is congruently arranged with the central longitudinal axes RL, BL such that the air supply is approximately symmetrical with respect to the body-fixation means 134a-d. Accordingly, the several body-fixation means 134a-d can be operated by air simultaneously.

Still referring to FIG. 2, in at least some embodiments, individual valves may be provided to individual ones of the body-fixation means 134a-d, the valves configured to be selectively opened and closed with regard to their airflow. In at least some embodiments, the individual valves may be selectively air controllable and/or selectively air operable. In at least some embodiments, the body-fixation means 134a-d having the individual valves may be configured to be selectively and/or individually controlled, especially in terms of supplying to and/or removing air from the body-fixation means. Further, the valves may, for example, be arranged between the frame structure 131 and the respective body-fixation means 134a-d, in particular instead of the attachment means 135a-d or together with the attachment means 135a-d, or within the frame structure 131.

Figure 3A:
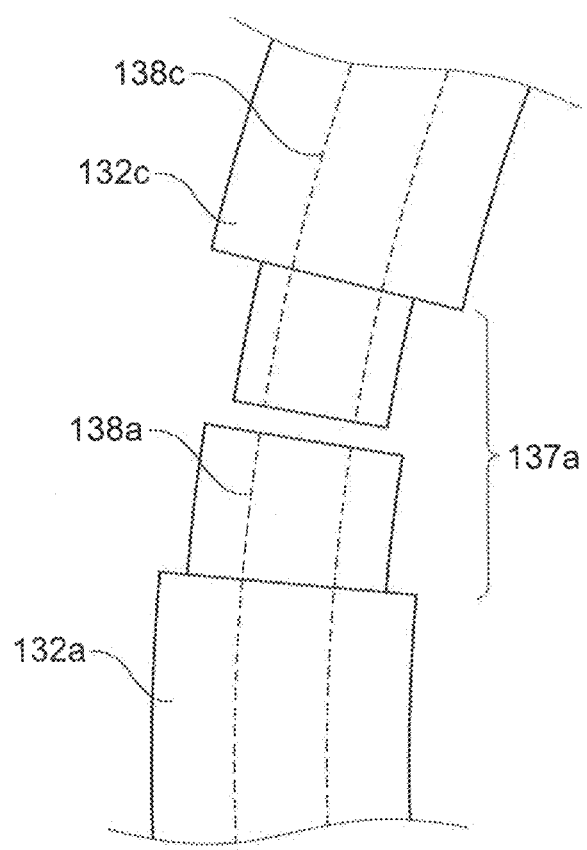
FIG. 3A is a partial section of two frame elements of a MR coil frame with a connecting portion for fluidically connecting the two frame elements to each other, according to an embodiment.

FIG. 3A illustrates schematically a partial section of the two frame elements 132a and 132c, i.e. the one frame leg with the cross connection, of the frame structure 131 with a connecting portion 137a-d for fluidically connecting the two frame elements to each other. In order to form the connecting portion 137a-d, the frame elements 132a-d are shaped and dimensioned so that they can be inserted into each other. As indicated by the dashed line, the frame elements 132a-d are hollow profiles forming an internal air duct 138a-d or a channel for passing an air tube. By releasing the frame elements 132a-d from each other, the air duct 138a-d is fluidically disconnected. In at least some embodiments, the individual valves of the body-fixation means 134a-d as described above may be arranged so as to interact with an associated one of the internal air ducts 138a-d or channels.

Figure 3B:
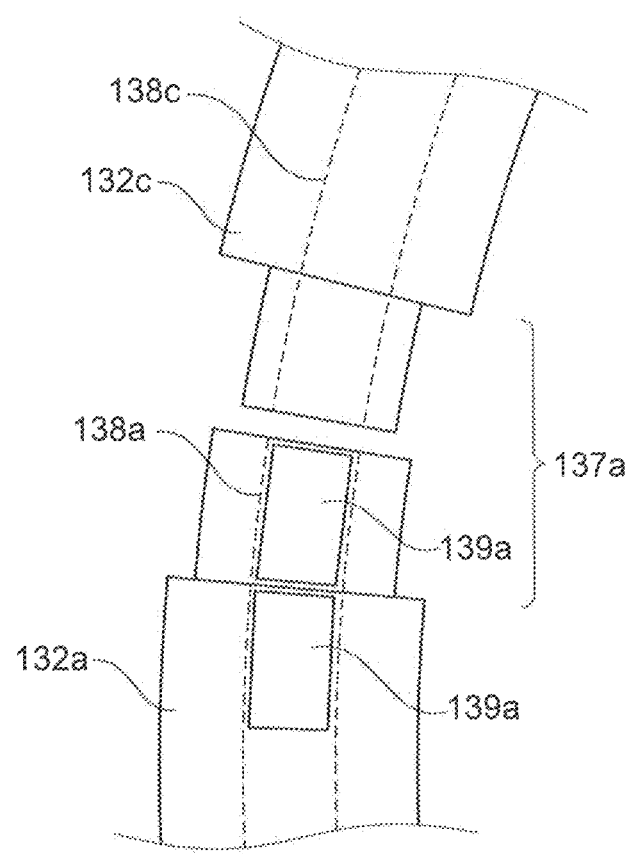
FIG. 3B is a partial section of two frame elements of a MR coil frame with a connecting portion for fluidically connecting the two frame elements to each other, according to a further embodiment.

FIG. 3B shows another embodiment, according to which at least one valve, blocking element and/or air blocker 139a-d is arranged in the internal air duct 138a-d, in order to avoid air leakage if the connecting portion 137a-d is not completely closed or otherwise leaking. As a result, with regard to the exemplary embodiment, only two of the four body-fixation means 134a-d can be evacuated simultaneously. In this embodiment, the two body-fixation means 134b and 134d arranged on the same side of the MR coil frame 130 can be evacuated simultaneously. Although two air blockers 139a are shown in FIG. 3B, one is sufficient in principle. The illustration in FIG. 3B is intended to illustrate only two exemplary possibilities for arranging the air blocker 139a-d. In at least some embodiments, the air blocker 139a-d may be used to provide the individual valve as described above.

Figure 4:
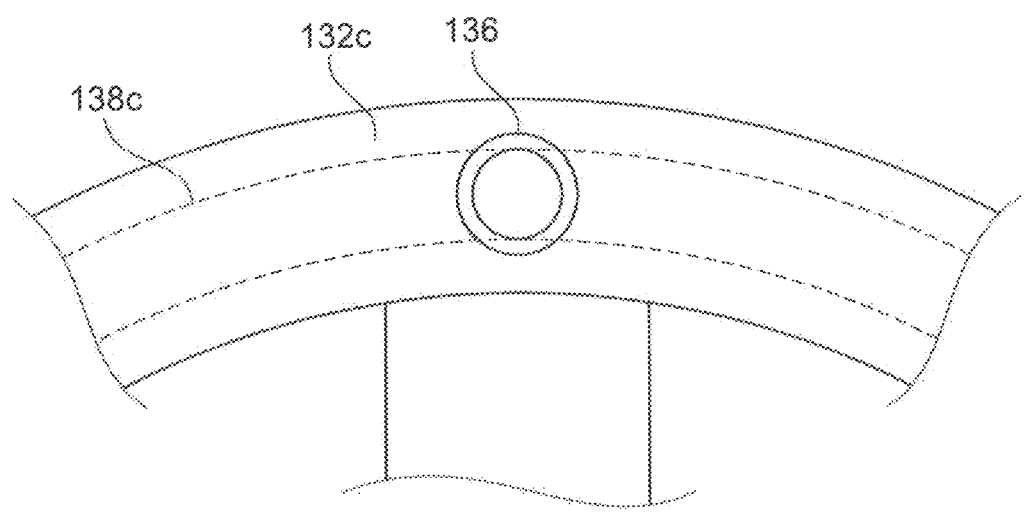
FIG. 4 is a partial section of a frame element of a MR coil frame, which section has a MR coil frame-sided connection piece for fluidically connecting a pumping device to the frame.

FIG. 4 shows schematically a partial section of the frame element 132c, at which the first connecting piece 136 for connecting the air supply of the air pumping device 150 is formed. The first connecting piece 136 is e.g. a plug-in or screw connection for easy connecting or disconnecting of the air supply, which is essentially formed by the air tube 151 of the air pumping device 150. As indicated by the dashed lines, the first connecting piece 136 opens into the internal air duct 138c of the frame element 132c. Thus, a fluidic connection to the other air ducts 138a, 138b and 138d is made via the frame element 138c.

Figure 5A:
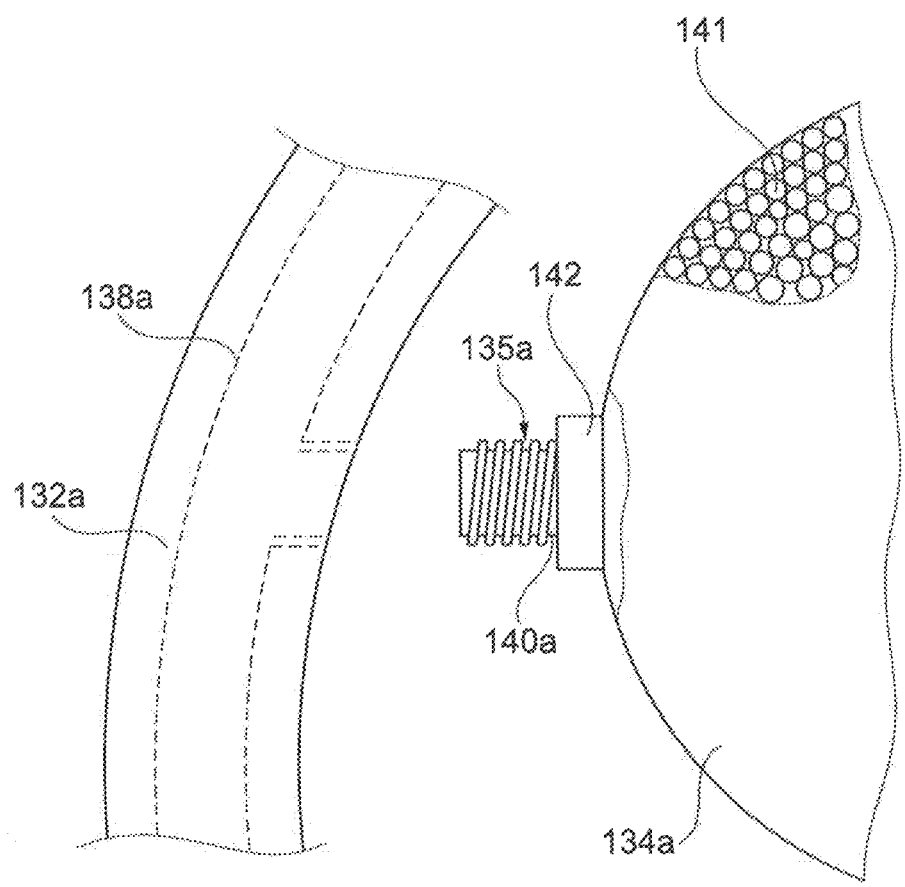
FIG. 5A is a partial section of a frame element of a MR coil frame and partial section of a body-fixation means which is being attached to the MR coil frame via a threaded connection, according to an embodiment.
Figure 5B:
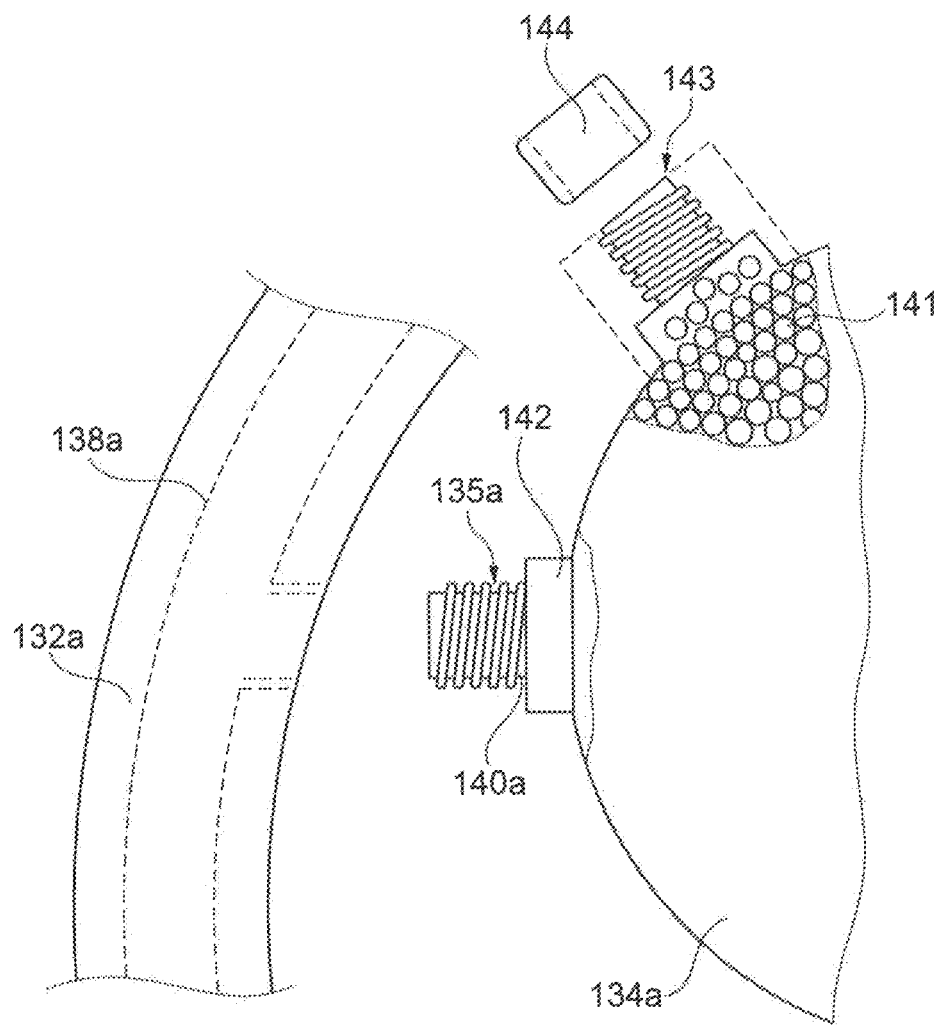
FIG. 5B is a partial section of a frame element of a MR coil frame and partial section of a body-fixation means which is being attached to the MR coil frame via a threaded connection, wherein the body-fixation means comprises a filling nozzle according to a further embodiment.

FIGS. 5A and 5B illustrate schematically a partial section of the frame element 132a carrying the body-fixation means 134a of FIG. 2, wherein the two parts are shown separately for better illustration. For attachment of the respective body-fixation means 134a-d, the corresponding frame element 132a-d has a MR coil frame-sided counterpart-attachment means, which is formed as an internal thread, as indicated by dashed lines. By way of example, the attachment means 135a-d is formed as a nut made from a non-conductive material, such as a suitable plastic material. It is embedded in the material of the respective body-fixation means 134a-d and has an external thread that is adapted in shape and dimensions to the internal thread of the frame element 132a-d. As shown, the respective attachment means 135a-d has an internal air duct 140a-d that forms a second connecting means. In this way, an internal volume of the respective body-fixation means 134a-d is fluidically connected to the air pumping device 150 via the respective air duct 140a-d of the or second connecting piece or attachment means 135a-d, the respective air duct 138a-d of the respective frame element 132a-d and the first connecting piece 136.

As mentioned above, the respective body-fixation means 134a-d is made from a flexible material and is formed as a vacuumable cushion having a variable shape or volume that may change due to the air operation. Accordingly, the shape or volume may change as the inner volume of the cushion is evacuated by the air pumping device 150. A material suitable for the body-fixation means 134a-d has air or gas tight, impermeable and/or insulating properties, such as foam, expanded polypropylene foam, polyurethane foam, polyamide foam, polyether ether ketone (PEEK) foam and biocompatible surface foam based on EVA (ethylene-vinyl acetate).

As shown in FIGS. 5A and 5B, the respective body-fixation means 134a-d is filled with a flowable filling material 141 which may be, for example, grains, balls or the like, preferably made of polystyrene or the like. Thus the body-fixation means 134a-d may ensure a conformal, patient specific mold. The type and/or quantity of the filling material 141 may vary in type and/or amount between the single body-fixation means 134a-d. In order to avoid suction of the filling material 141 through the internal air duct 140a-d by the air pumping device 150, an air filter 142 is arranged on an inner side of the air duct 140a-d adjacent thereto, which blocks the filling material 141, but nevertheless allows evacuation of the inner volume of the body-fixation means 134a-d.

As shown in FIG. 5B, in some embodiments, the body-fixation means 134a-d comprises a filling nozzle 143 that fluidically communicates with the internal volume of the body-fixation means 134a-d for filling the filling material 141. By way of example, the filling nozzle 143 has an external thread on which a cap 144 can be screwed to optionally open and close the filling nozzle 143. The filling nozzle 143 can also be embedded in the material of the body-fixation means 134a-d, for example by a multi-component injection molding. Thus, the user has the possibility to change the filling material 141 with respect to material type, ball size and amount such that the overall vacuum cushion stiffness, density, thickness, radiation beam attenuation, dose dosimetry can be adjusted by clinicians for different patients size as well as different body parts. Therefore, such personalized vacuum cushion can be used to reduce undesired radiation on different body parts for each patient case.

Starting from the illustrated embodiments above, the MR coil frame 130 according to the invention can be modified in many ways. For example, the frame elements 132a-d need not be airtight for directly guiding air. Rather, one or more air tubes (not shown) can be guided through the hollow frame elements 132a-d. Also, the attachment and second connecting means 135a-d need not necessarily be designed as an integral part, but can also be formed separately from each other. Furthermore, two or more frame-sided connecting pieces 136 can be provided if the body-fixation means are not to be air-operated via the common connecting pieces 136, e.g. when using the air blocker according to the embodiment as shown in FIG. 3B.

LIST OF REFERENCE SIGNS

100 MR-guided radiation system
110 MR scanner
120 support table
130 MR coil frame 131 frame structure
132a-d frame element
133 receiving space
134a-d body-fixation means
135a-d attachment means/second connecting piece
136 first (frame-sided) connecting piece
137a-d connecting portion
138a-d air duct
139a-d air blocker
140a-d air duct
141 filling material
142 air filter
143 filling nozzle
144 cap
150 air pumping device
151 air tube
160 RF coil
161 communication cable
LP patient's lying plane
BL (central) body longitudinal axis
RL (central) receiving space longitudinal axis

I claim:

1. A magnetic resonance coil frame, comprising
a frame structure, forming in between a receiving space for at least a body portion of a recumbent patient located in a lying plane,
wherein at least a first air-operated body-fixation means having a variable shape for immobilizing the body portion is arranged outside the lying plane at a side of the frame structure facing the receiving space,
wherein the frame structure has an internal air duct or a channel for passing an air tube, which air duct or air tube at least extends between a first air connecting piece for an air pumping device and an internal volume of the respective body-fixation means, and
wherein the frame structure comprises a plurality of frame elements being connected to each other and being formed as hollow profiles, the hollow profiles forming the internal air duct or channel such that the frame serves as a media supply for the body fixation means in order to air-operate the internal volume thereof.

2. The coil frame according to claim 1, wherein the frame structure carrying the body-fixation means bridge-like span the lying plane.

3. The coil frame according to claim 1, wherein relative to a longitudinal axis of the receiving space, which longitudinal axis is parallel to a body longitudinal axis of the patient to be immobilized, at least the first and a second body-fixation means are arranged at substantially opposing frame elements on sides thereof facing the receiving space.

4. The coil frame according to claim 3, wherein the first body-fixation means is arranged at a first frame leg protruding from the lying plane and the second body-fixation means is arranged at a second frame leg protruding from the lying plane, and wherein the first and second frame legs are arranged symmetrically with respect to the longitudinal axes.

5. The coil frame according to claim 1, wherein the first air connecting piece is arranged such that several of the body-fixation means can be operated by air simultaneously.

6. The coil frame according to claim 1, wherein the frame elements at least partially have a fluidically communicating connecting portion, via which the frame elements are detachably connected to each other.

7. The coil frame according to claim 6, wherein the internal air duct or the air tube is fluidically interrupted when the respective frame elements are disconnected.

8. The coil frame according to claim 1, wherein the at least first body-fixation means is fluidically connectable or connected to an air pumping device via a second air connecting piece.

9. The coil frame according to claim 1, wherein at least a portion providing the variable shape of the body-fixation means is formed from a flexible material having air or gas tight properties.

10. The coil frame according to claim 1, wherein at least a portion providing the variable shape of the body-fixation means is formed as a vacuumable cushion attachable to the frame structure.

11. The coil frame according to claim 10, wherein the vacuumable cushion is made of an impermeable and insulation material having a flowable filling material to ensure a conformal, patient specific mold.

12. The coil frame according to claim 11, wherein the body-fixation means has a filling nozzle communicating with an internal volume of the body-fixation means for filling the filling material.

13. The coil frame according to claim 1, wherein the body-fixation means is attached to the frame structure via at least one attachment means having an internal air duct or a channel for passing an air tube.

14. The coil frame according to claim 13, wherein the at least one attachment means is arranged on a side of the body-fixation means facing away from the receiving space.

15. The coil frame according to claim 13, wherein the at least one attachment means is a fastening nut made of a non-conductive material.

\* \* \* \* \*